United States Patent [19]

Klausz

[11] 4,236,081
[45] Nov. 25, 1980

[54] RADIOGRAPHIC APPARATUS

[75] Inventor: Rémy Klausz, Paris, France

[73] Assignee: Compagnie Generale de Radiologie, Paris, France

[21] Appl. No.: 8,410

[22] Filed: Feb. 1, 1979

[30] Foreign Application Priority Data

Feb. 7, 1978 [FR] France .................................. 78 03382

[51] Int. Cl.³ ...................... G01N 21/34; G01N 23/04
[52] U.S. Cl. .................................. 250/445 T; 250/360
[58] Field of Search ............ 250/360 R, 363 S, 445 T

[56] References Cited

U.S. PATENT DOCUMENTS 4,084,093  4/1978  Marsh et al. ...................... 250/445 T Primary Examiner—Alfred E. Smith
Assistant Examiner—Thomas P. O'Hare
Attorney, Agent, or Firm—Roland Plottel

[57] ABSTRACT

Radiographic apparatus reconstituting an image by processing by means of a computer the signals delivered by a detector measuring the coefficient of absorption of a body through which an X-ray beam passes.

A plurality of detectors disposed in a fan arrangement are used, whereby it is possible to decrease the number of scanning stations. According to the invention, this number of stations is an odd number for a complete revolution. Further, a number of detectors in excess is used for a given included angle of the fan arrangement so that the response of defective detectors can be eliminated.

2 Claims, 3 Drawing Figures

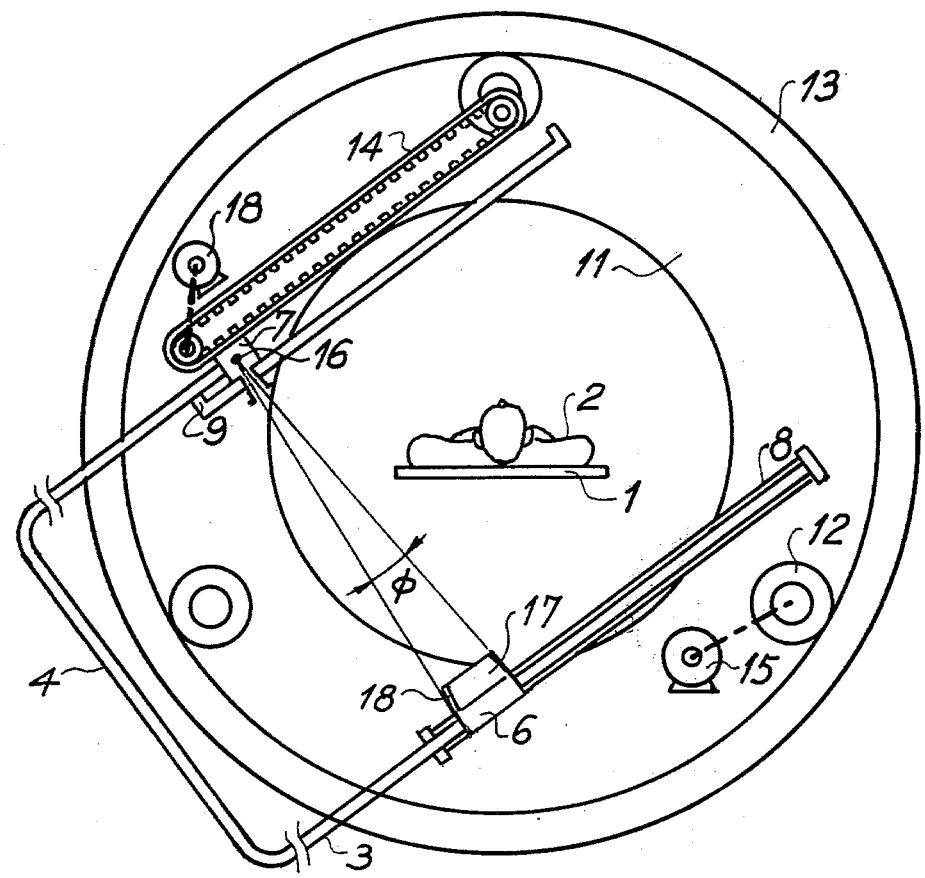
Fig_1

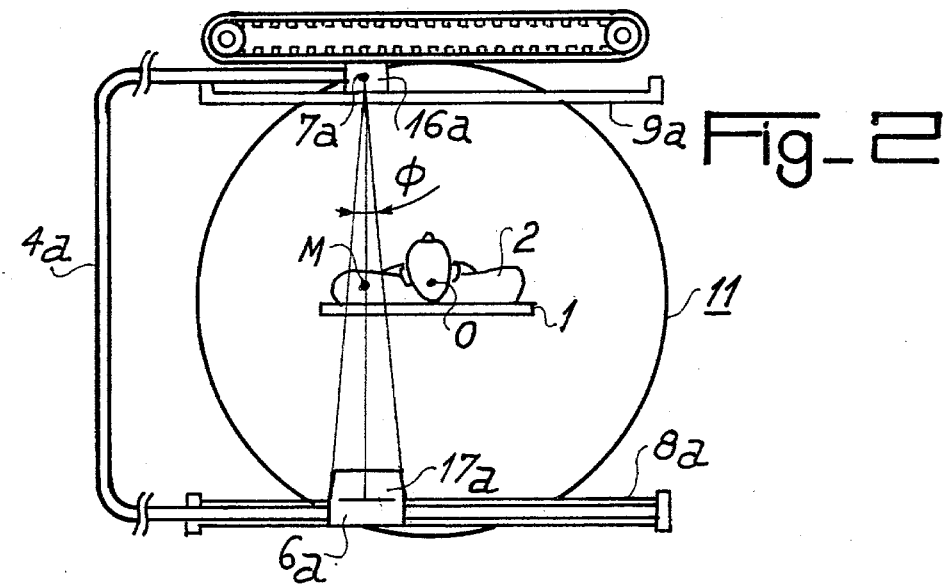
Fig_2
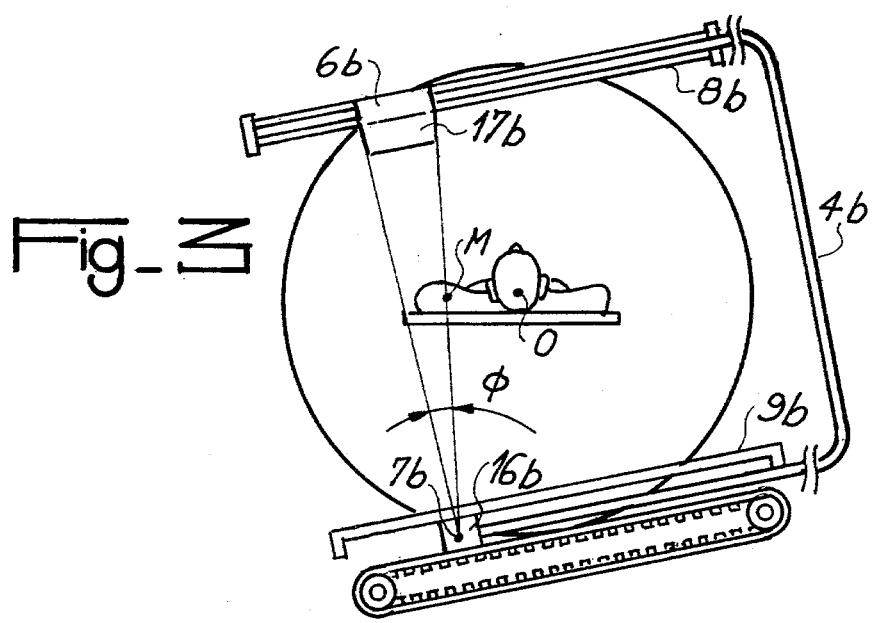
Fig_3

RADIOGRAPHIC APPARATUS

The invention relates to a radiographic apparatus and in particular an apparatus which reconstitutes the image by processing with a computer the signals furnished by a detector measuring the coefficient of absorption of a body through which passes a radiation beam moving in a plane, termed section plane.

Apparatus of this type, usually termed tomographic apparatus, comprise a source-detector assembly which moves and effects a scanning in the section plane; these scannings consist of a succession of linear translations effected at stations which are separated by elementary rotations in a plane parallel to the section plane. The measurements effected in the course of a translation constitute a parallel projection of the coefficients of absorption in a given direction, the reconstitution of an image requiring a certain number of projections which are equally spaced apart on a semi-revolution.

In other known apparatus, for the purpose of improving the utilization of the radiation emitted by the source, and increase the total number of photons employed, there are disposed in front of the source a plurality of detectors located in the section plane and spaced a predetermined angle apart and forming a fan arrangement the apex of which is the source.

It can be seen that, with this arrangement, there is obtained in the course of a translation a number of projections equal to the number of detectors.

If:

$\alpha$ the angle between two detectors, $\phi$ the angle of rotation of the mechanical unit carrying the fan arrangement and its system for moving it in translation between two stations, $\theta$ the angle between the directions of two successive projections, n the number of projections equally spaced apart on a semi-revolution required for reconstituting a correct image, p the number of detectors.

The angle between the directions of two successive projections is therefore:

$$\theta = 180/n$$

The (n+1) th projection is therefore made with an angle identical to the first, but with an opposite direction of propagation of the radiation. The number of mechanical positions, or stations, required to obtain the n projections depends on the relative values of $\alpha$, $\theta$ and n. Generally, $\alpha$ is made equal to $\theta$ (the angle between two detectors being equal to the desired angle between two successive projections) and we then have:

$$\phi = p\,\alpha$$

This angle is equal to the included apex angle of the fan arrangement. Thus it can be seen that the angle of rotation between two stations increases with the number of detectors used. In this way, the number of stations, and consequently the time required to obtain n projections, is reduced. This advantage is usually used to decrease this time and improve the performance of the apparatus. For this purpose one does not limit oneself to n projections in a semi-revolution, but 2n projections in a complete revolution or even more are effected. A mean value is taken of the measurements made by the detectors at 180°. This permits, at least partly, overcoming various drawbacks, and in particular those presented by the non-parallelism of the radiation beam and by the "self-hardening" phenomenon of the radiation beam caused by the priority absorption of the soft rays by the peripheral masses of the body to be examined.

But other drawbacks remain, and in particular those due to defects of the detectors, to their unreliability over a period of time, and to the differences of response from one detector to another for a given magnitude to be measured.

An object of the invention is to provide a radiographic apparatus which overcomes these last mentioned drawbacks.

According to the invention, on one hand, it is arranged that the measurements made at 180° are made by different detectors for each point of the section plane and, on the other hand, by comparing the measurements made by two neighboring detectors, by eliminating the abnormal measurements, the measurements of the end detectors are compared with those of additional detectors disposed at the ends of the fan arrangement.

The radiographic apparatus according to the invention comprises a support for the body to be examined, a device mounted to be movable in rectilinear translation on a frame mounted to be rotatable about the support, the device carrying a source emitting a radiation in the direction of a plurality of detectors fixed thereon, on the opposite side of the support to the source, in a section plane which is substantially perpendicular to the axis of rotation of the frame. These detectors are arranged in a fan arrangement relative to the source which constitutes the apex and the frame, which is rotatable, has a plurality of immobilization stations in which the device moves in translation, the angle between two neighboring stations being equal to the included angle of the fan arrangement and being different from a sub-multiple of a semi-revolution.

With this arrangement, the measurements effected at 180° at all points of the section plane are never effected by the same detector. By combining the opposite measurements it is thus possible to at least partly remedy the breakdown of a detector.

According to another feature of the invention, at least one end of the fan arrangement of the detectors comprises an additional detector.

The responses of these additional detectors are compared with the responses of the other detectors and, in the event of a breakdown of one thereof revealed by this comparison, it is possible to replace these measurements by those of the additional detector which cross-check them.

Other features will be apparent from the ensuing description of an embodiment with reference to the accompanying drawings in which:

FIG. 1 is a cross-sectional view of the apparatus, and

FIGS. 2 and 3 are simplified diagrammatic sectional views of the positions of the movable device at two stations.

FIG. 1 shows a support 1 which is fixed to a stand (not shown) and on which is placed a body 2 to be examined. A device 3, formed by a U-shaped member 4 carrying at the ends of its two branches slideblocks 6 and 7, slides in slideways 8 and 9 which are secured to a circular frame 11 which rolls by means of rollers 12, rotated by a motor 15, inside a circular rail 13 fixed to the stand. A toothed belt 14 driven by a motor 18 is fixed to the frame 11 and moves the slideblocks 6 and 7 along the slideways 8 and 9. The source of radiation 16 is fixed to the slideblock 7; it irradiates a unit having a plurality of detectors 17 fixed to the slideblock 6 in emitting a fan-shaped radiation beam having an included angle φ.

In a preferred arrangement, this angle is 12° and the detectors are 31 in number one of which is the additional detector. The measurements effected by the detectors are sent to a computer (not shown) for processing.

In operation, with the frame 11 immobilized in a given position, the motor 18 moves the device 3 with respect to the frame 11. During this rectilinear scanning, the detectors furnish the data of P projections, p being the number of detectors and the projections being angularly spaced apart by an angle α.

Subsequent to this translation, the motor 15 drives in rotation the frame 11 and the device 3 to a new station where a second scanning will take place. The angle φ of rotation between two stations is taken to be equal to the included angle of the fan arrangement.

In order to explain the invention there is diagrammatically shown in FIGS. 2 and 3 a section of the apparatus with the device 3 in two positions a and b which are substantially opposed. The index a (FIG. 2) added to the reference numerals corresponds to the original station and the index b (FIG. 3) to the substantially opposed station. Only the inner part of the frame 11 has been shown.

Let M be a considered point of the body 2 to be examined. In a first station the point M has a vertical ray passing therethrough. In the case of FIG. 2, the detector which receives the beam is that which is disposed in the middle of the unit 17a of the detectors. After a certain number of stations angularly spaced apart an angle equal to φ, the fan arrangement is at the station where the scanning causes a vertical ray to pass through the point M but in the opposite direction to the former direction. This station has the index b (FIG. 3).

According to a feature of the invention, this station, which provides an irradiation of the point M in the opposite direction, does not correspond in respect of the frame 11, to a position which is symmetrical relative to the initial position.

In other words, the angle φ defined by two neighboring stations is different from a sub-multiple of a semi-revolution. Consequently, the detector which receives the vertical ray in the inverse position is different from that which received it in the initial position.

FIGS. 2 and 3 show the case where the angle φ is an odd sub-multiple of a revolution. The concerned detector in the initial position is that of the middle; in the inverse position, the concerned detector is that which is located at one end of the fan arrangement.

It can be seen that this change of detectors for measurements of the same direction enables the breakdown of a detector to be eliminated or remedied.

According to another feature of the invention, an additional detector 18 (FIG. 1) is added to the detectors unit 17. As mentioned herein before, its responses are compared with those of the other detectors in closely similar positions and the responses of a detector which shows itself to be defective are eliminated.

What is claimed is:

1. In a radiographic apparatus comprising:
   a support for receiving a body to be examined,
   a device mounted to be movable in rectilinear translation on a frame mounted to be rotatable about the support, said device carrying a source emitting an X-ray beam in the direction of a unit having a plurality of detectors said detectors being fixed on said device, on the opposite side of the source and in a plane substantially perpendicular to the axis of rotation of the frame, the support being disposed between said source and said detectors, said detectors being disposed in a fan arrangement relative to the source which constitutes the apex thereof, the rotatable frame having a plurality of immobilization stations at which the device moves in translation, the angle defined between two neighboring stations being equal to included angle of the fan arrangement,
   the improvement consisting in the angle defined between two neighboring stations, which is an odd fraction of a revolution.

2. A radiographic apparatus as claimed in claim 1 wherein the unit having a plurality of detectors disposed in a fan arrangement relative to the source, comprises coupled at least to one of its ends, an extra detector, in addition to said plurality of detectors, the responses of said extra detector compared with those of the plurality of detectors in closely similar positions and in the event of a breakdown of one thereof revealed by this comparison. The measurements of the broken down detector being replaced by those of said extra detector.

* * * * *